United States Patent [19]
Kan et al.

[11] Patent Number: 6,094,590
[45] Date of Patent: Jul. 25, 2000

[54] SURGICAL OPERATING APPARATUS

[75] Inventors: Kazutoshi Kan, Ibaraki-ken; Masakatsu Fujie, Ushiku; Ryuichi Shinomura, Higashimatsuyama; Koichi Sano, Yokohama; Hiroshi Takeuchi, Matsudo, all of Japan

[73] Assignee: Hitachi, Ltd., Tokyo, Japan

[21] Appl. No.: 08/932,920

[22] Filed: Sep. 18, 1997

[30] Foreign Application Priority Data

Sep. 18, 1996 [JP] Japan .................................. 8-245919

[51] Int. Cl.$^7$ ........................................................ A61B 8/00
[52] U.S. Cl. ................................................................ 600/411
[58] Field of Search .................................... 600/411, 415, 600/427; 324/318; 5/600, 601

[56] References Cited

U.S. PATENT DOCUMENTS

| | | | |
|---|---|---|---|
| 5,207,223 | 5/1993 | Adler | 600/411 |
| 5,525,905 | 6/1996 | Mohapatra et al. | 342/318 |
| 5,526,814 | 6/1996 | Cline et al. | . |
| 5,748,767 | 5/1998 | Raab | 604/411 |
| 5,823,960 | 10/1998 | Young et al. | 600/415 |

FOREIGN PATENT DOCUMENTS

| | | |
|---|---|---|
| 0 314 262 | 5/1989 | European Pat. Off. . |
| 42 13 426 | 10/1992 | Germany . |
| 95/16396 | 6/1995 | WIPO . |

*Primary Examiner*—Marvin M. Lateef
*Assistant Examiner*—Maulin Patel
*Attorney, Agent, or Firm*—Antonelli, Terry, Stout & Kraus, LLP

[57] ABSTRACT

A surgical operating apparatus capable of a high-precision surgical operation while observing a detailed image of an affected part to be subjected to surgical operation and capable of observing a related location of the affected part under surgical operation by means of an image obtained the imaging of a wider range is provided with an operating table provided in an area made an object of measurement by an MRI apparatus so that a surgical operation can be performed by operating an operating manipulator by an operation input device while monitoring a local image from an endoscope and/or a ultrasonic scanner and the observation of a range in the neighborhood of the affected part and wider than an observing area of the endoscope is enabled by the MRI apparatus under surgical operation, thereby providing a high-security surgical operating apparatus.

16 Claims, 8 Drawing Sheets

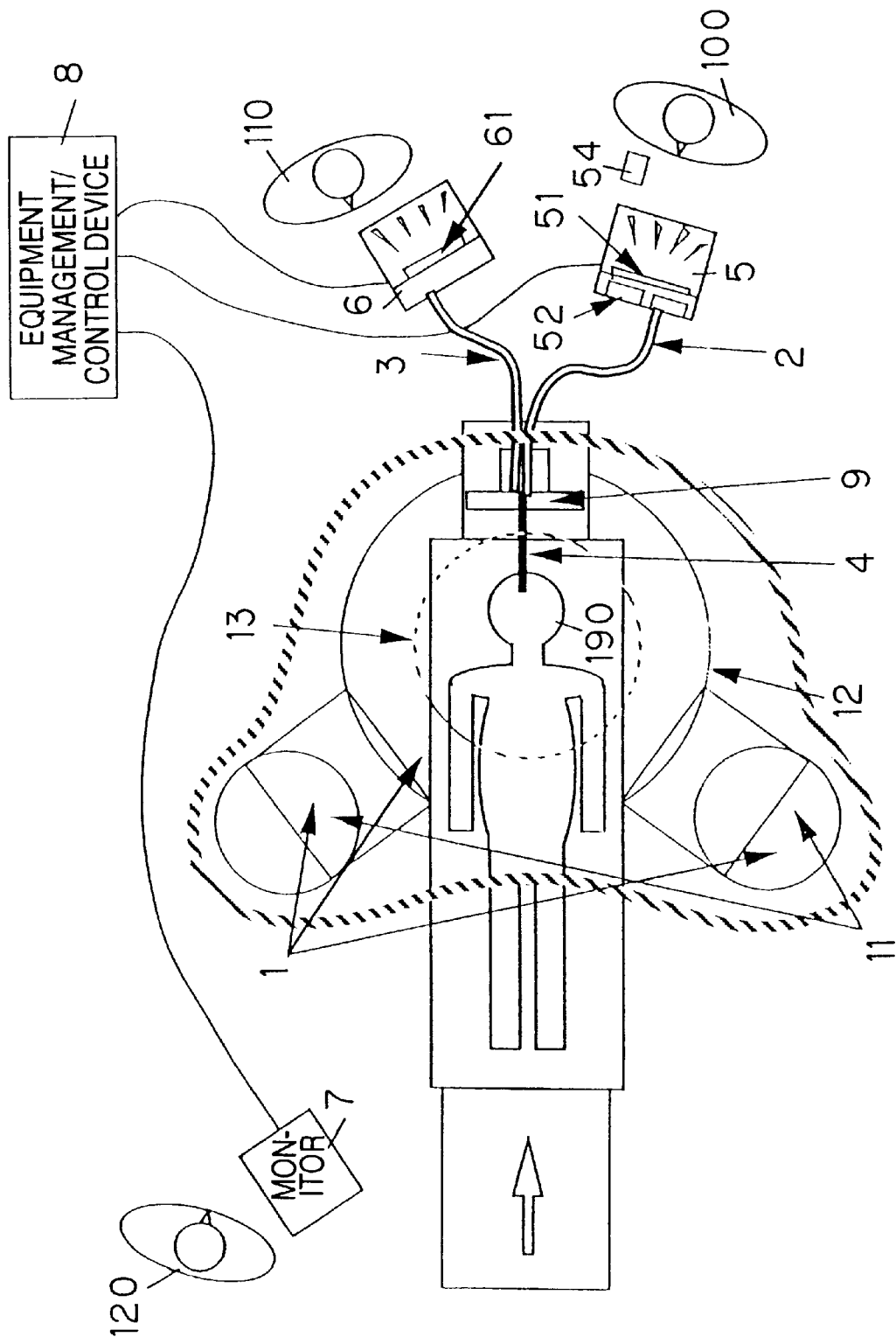

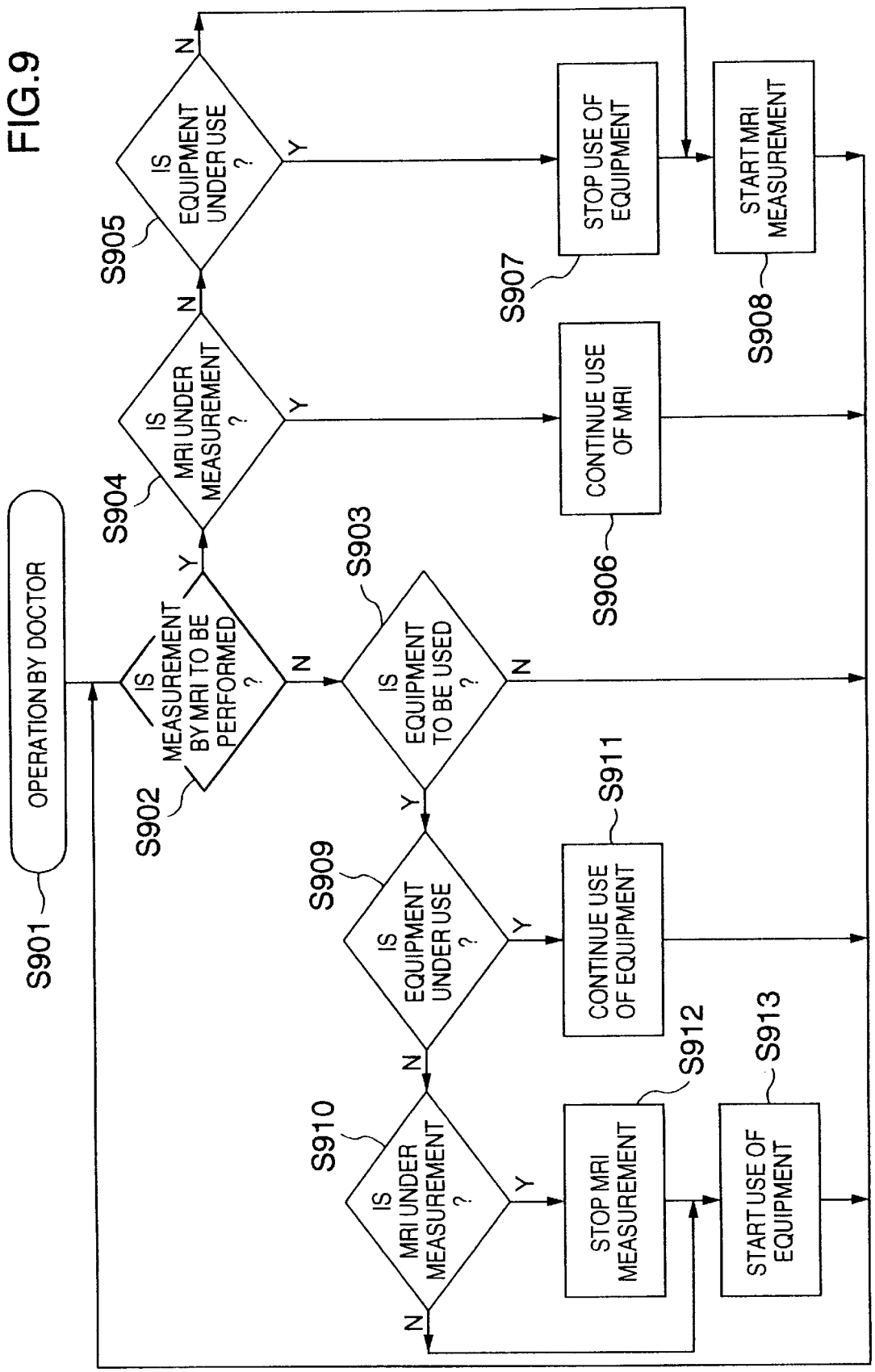

SURGICAL OPERATING APPARATUS

BACKGROUND OF THE INVENTION

The present invention relates to a medical equipment or medical facility which enables a medical care or surgical operation on the same operating table by use of information obtained by a magnetic resonance imaging (MRI) apparatus and information obtained by unit such as an endoscope for imaging a local portion.

JP-A-7-194616 has proposed a surgical operation supporting system in which the inserted state of an interposition such as a catheter inserted into an object to be inspected can be confirmed in real time, thereby making it possible to correctly perform an inserting operation of the interposition. This surgical operation supporting system is provided with a bed having a top table capable of small movement and an X-ray tomographic imaging apparatus (or X-ray CT apparatus) and can generate a tomographic (or cross-sectional) image or three-dimensional image of the object fixed on the top table.

Further, JP-A-8-140958 has proposed a medical care under an inspecting environment using an open gantry MRI apparatus.

Also, JP-A-7-194609 has proposed an apparatus in which a medical care is performed utilizing a master/slave manipulator for medical use and an endoscope.

Thus, there have been proposed the systems enabling the measurement or inspection of an affected part in a body non-incursively from the outside of the body and the apparatuses aiming at a minimally invasive operation in which a surgical operation can be performed with no large cut of the body surface.

In the surgical operation supporting system disclosed by the JP-A-7-194616 as the above-mentioned prior art, a three-dimensional measurement is possible in a noninvasive manner for a patient but the use of the supporting system for a surgical operation is not taken into consideration. Since there may be the case where the surgical operation is performed over a long time, it is necessary that the imaging of an affected part can be performed over the long time. Also, it is necessary that a detailed image of particulars can be obtained. In the case of the X-ray CT apparatus, there is a problem of exposure of medical staffs and hence it is difficult to continue the measurement over a long time during a surgical operation. Also, it is difficult to obtain a detailed image of an affected part which is required for the surgical operation (or such an image as seen with the naked eyes).

In the case where an X-ray CT apparatus is used as a surgical operation supporting system, it is general as the way of use that the inspection of an affected part is performed by the X-ray CT apparatus before a surgical operation and the effect of the surgical operation is confirmed by performing the inspection by use of the X-ray CT apparatus again after the surgical operation. However, in the case where the effect of the surgical operation could not be confirmed as the result of the inspection after the surgical operation, a surgical operation will be needed again. This imposes a large load on both a patient and a doctor.

In the case where the open configurated gantry MRI apparatus disclosed by the JP-A-8-140958 is used for a surgical operation, the problem of exposure of medical staffs during the surgical operation over the long time can be solved. However, it is still difficult to obtain the detailed image of an affected part which is required for the surgical operation (or such an image as seen with the naked eyes). Further, the JP-A-8-140958 shows that a medical care is performed by a doctor at a place which is very close to the MRI apparatus. However, when considering an unexpected accident caused by a high-strength magnetic field or any influence as in the case where a metal is brought carry by any chance, it is preferable that the surgical operation can be performed by the doctor without getting near the MRI apparatus.

In the case where a minimally invasive operation is performed by use of the manipulator disclosed by the JPA-7-194609, the neighborhood of a working area of the manipulator is observed by an endoscope without largely cutting the body surface at a surgical operating position. In this case, the field of view of the endoscope is narrow or it is only a very limited range of a surgical operating area which can be observed. Therefore, it is not possible to observe the surgical operating area or an affected part in a wide range.

Also, even if an apparatus or system capable of an advanced medical treatment is contrived, the security takes preference of the whole, at the scene of medical treatment. Therefore, also in a surgical operating apparatus in which diagnostic techniques and manipulators are freely used, it is important to keep the security.

SUMMARY OF THE INVENTION

An object of the present invention is to provide a surgical operating apparatus in which a surgical operation is enabled with a high precision by obtaining a detailed image of an affected part while the surgical operation is enabled with a high security by making it possible to observe a related location of the affected part by use of an image obtained by the imaging of a wider range.

To attain the above object, the present invention provides a surgical operating apparatus comprising an operating manipulator for supporting a surgical operating equipment, operation input unit for operating the operating manipulator, imaging unit for locally observing a working area of the surgical operating equipment, and an operating table, in which a magnetic resonance imaging apparatus having a range wider than a viewing field of the imaging unit as an area made an object of measurement is provided, and the operating table is arranged so that the area made the object of measurement by the magnetic resonance imaging apparatus is positioned on a surface of the operating table, whereby the measurement by the magnetic resonance imaging apparatus and a surgical operation based on the surgical operating equipment supported by the operating manipulator are enabled on the operating table.

The surgical operating equipment supported by the operating manipulator may be arranged so that it is operated in the area made the object of measurement by the magnetic resonance imaging apparatus.

It may be constructed such that the operating manipulator and the imaging unit are supported by a support and the support is provided so that it is movable relative to the operating table in a longitudinal direction of the operating table.

It may be constructed such that the operating manipulator and the imaging unit are supported by a support and the support is provided on a side portion of the operating table along a longitudinal direction of the operating table.

The support for supporting the operating manipulator and the imaging unit may be provided detachably.

A console provided with the operation input unit may be arranged so that the console and the operating manipulator exist in the angle of visibility of an operator who operates the operation input unit.

The console provided with the operation input unit may be arranged so that the operating manipulator exists on a side more back than a front face of the console.

The console provided with the operation input unit may be is arranged so that the operating manipulator exists on a side more back than the foremost portion of the console.

It may be constructed such that the magnetic resonance imaging apparatus includes cylindrical magnetic generators which are provided parting up and down and pillars which support the magnetic generators so that an interval therebetween is kept, the operating manipulator and the imaging unit are supported by a support, and a console provided with the operation input unit is arranged on the support side relative to the pillars in a longitudinal direction of the operating table.

To attain the above object, the present invention also provides a surgical operating apparatus comprising an operating manipulator for supporting a surgical operating equipment, operation input unit for operating the operating manipulator, imaging unit for locally observing a working area of the surgical operating equipment, and an operating table, in which a magnetic resonance imaging apparatus having a range wider than a viewing field of the imaging unit as an area made an object of measurement is provided, the operating table is arranged so that the area made the object of measurement by the magnetic resonance imaging apparatus is positioned on a surface of the operating table, and a control device for making a change-over between a measuring mode by the magnetic resonance imaging apparatus and an operating mode of the surgical operating equipment is provided to perform the measurement by the magnetic resonance imaging apparatus and the operation of the surgical operating equipment exclusively from each other, whereby the measurement by the magnetic resonance imaging apparatus and a surgical operation based on the surgical operating equipment supported by the operating manipulator are enabled on the operating table.

The imaging unit provides the display (or monitoring) of a detailed image of a very limited range of a surgical operating area, thereby supporting the operation by an operator which performs a surgical operation. The operator can perform a surgical operation requiring a high precision while observing the detailed image. Also, since an image of an area wider than the image obtained from the imaging unit can be obtained from the magnetic resonance imaging apparatus under the surgical operation, it is possible to promptly cope with even a change or problem (or trouble) outside of the viewing field of the imaging unit.

An example of such imaging unit includes an endoscope and a display for displaying an image obtained through the imaging by the endoscope.

BRIEF DESCRIPTION OF THE DRAWINGS

FIG. 8 is a diagram for explaining the arrangement in a fifth embodiment of the present invention; and FIG. 9 is a flow chart showing a change-over between an MRI measurement and the operation of a surgical operating equipment in a surgical operating apparatus according to the present invention.

DESCRIPTION OF THE PREFERRED EMBODIMENTS

Embodiments of the present invention will be described using the accompanying drawings.

Figure 1:
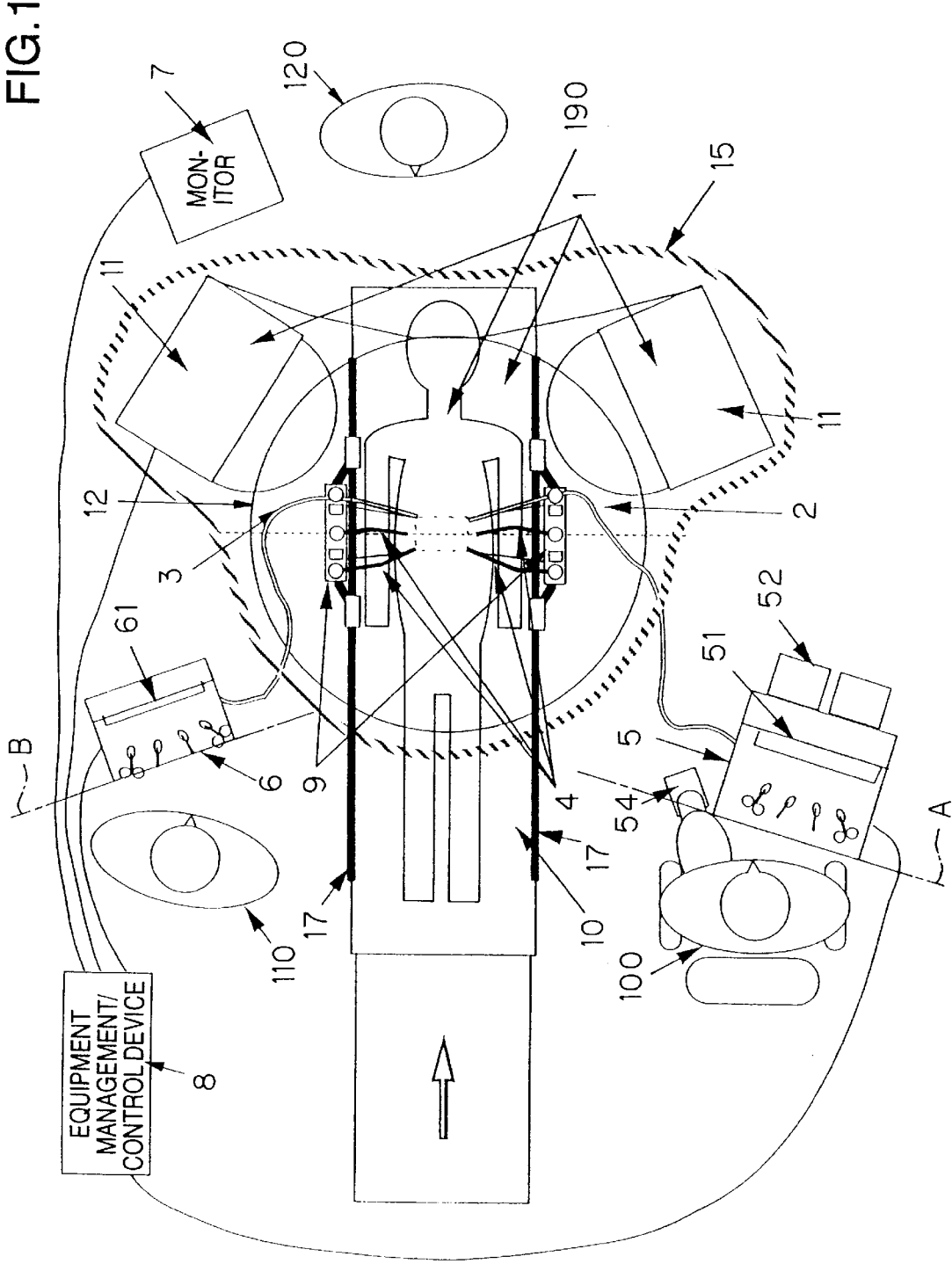
FIG. 1 is a diagram for explaining the arrangement in a first embodiment of the present invention.

FIG. 1 shows a first embodiment in which an open configurated gantry MRI apparatus 1 is used such that an operating table 10 is provided in an area made an object of measurement by the MRI apparatus 1.

The MRI apparatus 1 includes two substantially cylindrical magnetic generators 12 which are provided parting up and down, pillars 11 which support the magnetic generators 12, and an MRI controller (not shown) which controls the magnetic generators 12. The area made the object of measurement by the MRI apparatus 1 is a space in an area of a uniform magnetic field sandwiched between the magnetic generators 12 and is established in the vicinity of the center of a circle of the cylindrical form.

The operating table 10 can be taken in and taken out in parallel to a longitudinal direction of the operating table, as shown in FIG. 1, in order that a surgical operating position including an affected part is brought into the area made the object of measurement by the MRI apparatus 1. Thereby, it is possible to easily adjust the position of the affected part.

A supporting device 9 serves for an abdominal wall lifting device, too. Namely, the supporting device 9 serves, as a device for lifting a body surface tissue, to lift an abdominal wall for ensuring a surgical operating field. At the same time, the supporting device 9 supports mechanism which is capable of entering an endoscope unit and an ultrasonic scanner unit 3 into the affected part and controlling the positions/postures thereof from the exterior. Further, the supporting device 9 supports operating manipulators 4 which are capable of entering tools for medical treatment into the affected part for a surgical operation and controlling the positions/postures thereof from the exterior.

The endoscope 2 is controlled by an endoscope controller provided on a console 5 to obtain an image of the affected part. Similarly, the ultrasonic scanner unit 3 is controlled by an ultrasonic scanner controller provided on a console 6 to obtain an ultrasonic image of the interior of the body such as internal organs. It is not necessarily required that the endoscope controller and the ultrasonic scanner controller be provided independently on the consoles 5 and 6. Those controllers may be provided together on one of the consoles 5 and 6 on the near side to the endoscope or the ultrasonic scanner or may be provided on an equipment management/control device 8.

The operating manipulator 4 is attached at its tip with a tool for medical treatment such as forceps, laser knife or the like. The position/posture of the tool for medical treatment is controlled from the console 5 or 6 with an external operation input device in accordance with the operation of the operation input device by a doctor.

A term "surgical operating equipment" referred to herein represents an equipment which has a manipulator function capable of being moved remotely in accordance with an operation input by a doctor and has a tool for surgical operation at a tip thereof. Namely, it may include the endoscope unit and the ultrasonic scanner unit the position/posture of each of which can be controlled from the exterior, and the manipulator provided with the tool for medical treatment such as forceps, laser knife or the like the position/posture of which can be controlled from the exterior.

Accordingly, the doctor's intension is taken in the form of a change in position or posture so that the position or posture of the surgical operating equipment is controlled in accordance with the change information. Thus, a so-called master/slave manipulator system is formed. The surgical operating equipment or a device for supporting a tool for surgical operation is provided with means for detecting a tactile sense or a force so that information of a force or a tactile sense received by the surgical operating equipment from a tissue is returned to the operation input device operated by the doctor as feedback.

Imaging devices such as the endoscope unit 2 and the ultrasonic scanner unit 3 are provided as local imaging units. The endoscope 2 is supported by a supporting device capable of changing the position/posture of the endoscope 2 so that the position or posture of the endoscope 2 is changed in accordance with an instruction from a doctor, as desired by the doctor. Similarly, the ultrasonic scanner 3 is supported by a supporting device capable of changing the position/posture of the ultrasonic scanner 3 so that the position or posture of the ultrasonic scanner 3 is changed in accordance with an instruction from a doctor, as desired by the doctor.

The supporting device 9 is attached to opposite sides of the operating table 10 along the longitudinal direction thereof. In the case where the MRI apparatus 1 is used only for the purpose of inspection, the supporting device 9 can be detached. Also, guide rails 17 are provided on the opposite sides of the operating table 10 along the longitudinal direction thereof so that the supporting device 9 can be moved to the optimum position in compliance with a location of a patient 190 to be subjected to surgical operation (or the affected part).

The main console 5 is used by a main operator 100. The main console 5 is provided with an operation input device for operating the operating manipulators 4 and a display device for displaying a tomographic (or cross-sectional) image from the MRI apparatus 1, an image from the endoscope 2, an ultrasonic image and the other medical information. Further, an MRI image before a surgical operation and guidance information are displayed. A stereoscopic monitor 51 can display information from the MRI apparatus and a three-dimensional version of the ultrasonic image stereoscopically. Also, a sub-monitor 52 is a monitor for displaying the cross-sectional image or the ultrasonic image. A change-over between the images can be conducted using a pedal or the like without using a hand.

The auxiliary console 6 is used by an assistant operator 110. The auxiliary console 6 is provided with a function equivalent to the main console 5. The auxiliary console 6 has an operation input device which the assistant operator operates the operating manipulators 4 in lieu of the main operator and a monitor 61 for image display.

A medical information monitor 7 is mainly used by an anaesthetist doctor 120. The medical information monitor 7 is used as a monitor for the maintenance of the life of the patient and for vital functions thereof.

The equipment management/control device 8 is connected to each device in the surgical operating apparatus so that it makes the communication of data with each device and the monitoring of the function of each device. In the case where an abnormality is generated, the equipment management/control device 8 informs the medical staffs of the abnormality and stops the device promptly, as required.

Figure 2:
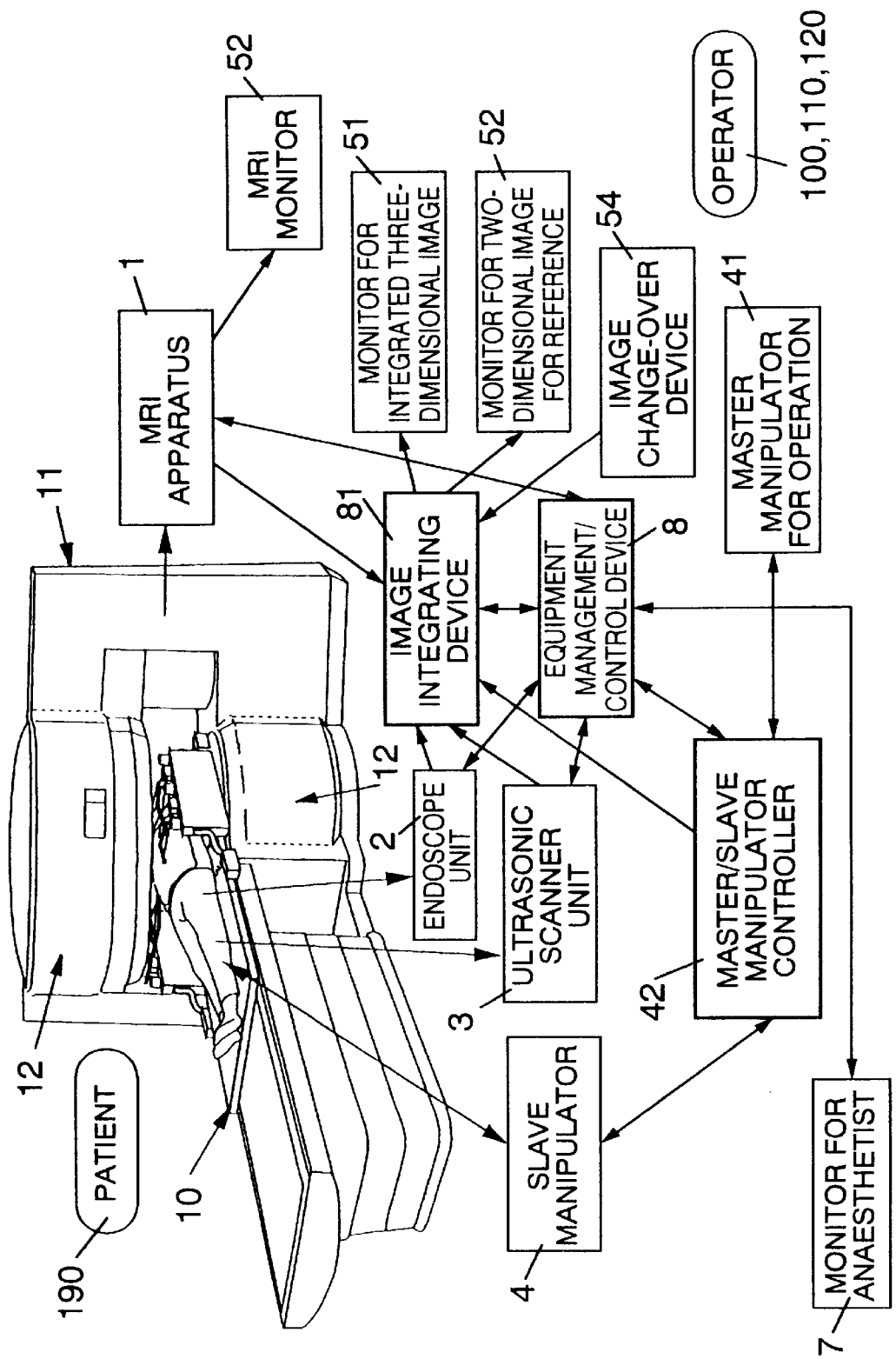
FIG. 2 is a block diagram showing the construction of the first embodiment of the present invention.

FIG. 2 shows, in a conceptual construction, the present embodiment together with the external appearance of the open gantry MRI apparatus 1. Information from the open gantry MRI apparatus 1 is not only directly displayed as an image on the sub-monitor 52 but also inputted to an image information integrating or combining device 81. Also, an endoscope image from the endoscope 2 is inputted to the image information integrating device 81. Further, image information from the ultrasonic scanner 3 is inputted to the image information integrating device 81. These images are reconstructed by the image information integrating device 81 and the reconstructed image is displayed as a three-dimensional image on the stereoscopic monitor 51. A change-over between images is made by the image information integrating device 81 in accordance with a signal from an image change-over device 54 such as a pedal.

Also, the operating manipulator 4 is controlled in position/posture by an operating manipulator controller 42 in accordance with information of an operation by the doctor from an operation input device 41 that is a master manipulation for operation input.

The MRI apparatus 1, the endoscope 2, the ultrasonic scanner 3, the image information integrating device 81, the operating manipulator controller 42 and the medical information monitor 7 are connected to the equipment management/control device 8 which in turn makes the communication of information with each equipment and the monitoring of any abnormality of each equipment.

Figure 3:
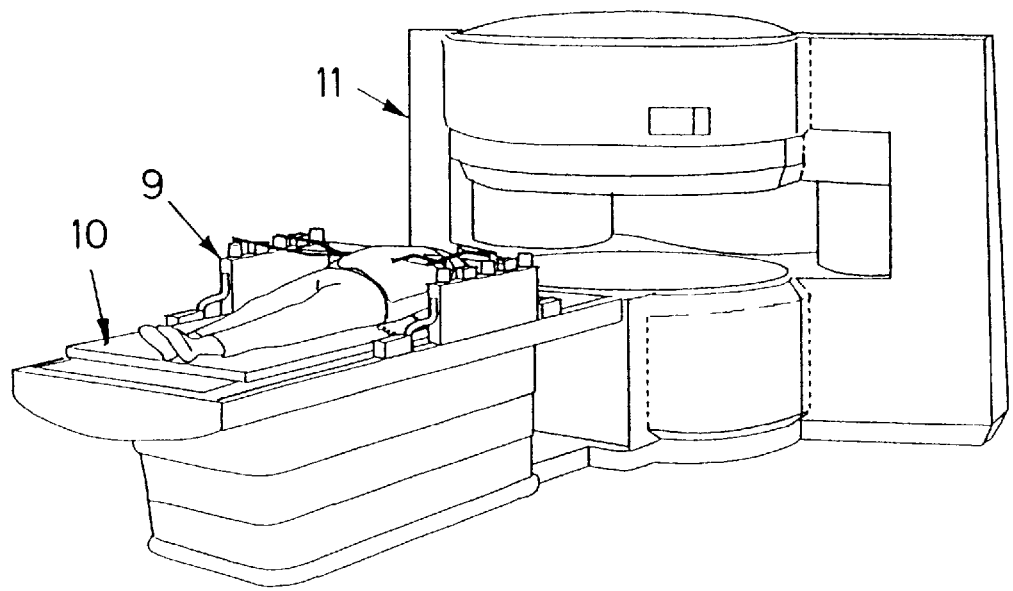
FIG. 3 is a diagram for explaining a state before a surgical operation in the first embodiment of the present invention.

Prior to a surgical operation in the present embodiment, the patient is fixed on the operating table 10 at a position taken out of the area made the object of measurement by the MRI apparatus and the supporting device 9 is moved to the optimum position for a surgical operating position of the affected part and is fixed to the operating table (see FIG. 3). Next, a body surface tissue is lifted for ensuring a surgical operating field of the affected part. This is performed in a manner that a plurality of holes are provided through the body surface (mainly, abdominal wall or the like) and abdominal wall lifting members provided in the supporting device 9 are inserted into the holes to lift the abdominal wall above. The abdominal wall is fixed in the lifted state. Further, the endoscope 2, the ultrasonic scanner 3 and the operating manipulators are inserted from small holes which are similarly provided in the body surface. For this purpose, there may be used the insertion holes for the abdominal wall lifting members. In order to make the incursion into the body surface as small as possible, it is preferable that the insertion holes for the abdominal wall lifting members and the insertion holes for surgical operating equipments such as the endoscope, the ultrasonic scanner and the operating manipulators are used in common. Thereby, for example, six holes in total suffice for a surgical operation which uses one endoscope, one ultrasonic scanner and four operating manipulators. Further, sensors for life maintenance and living body monitoring are attached to the patient.

Figure 4:
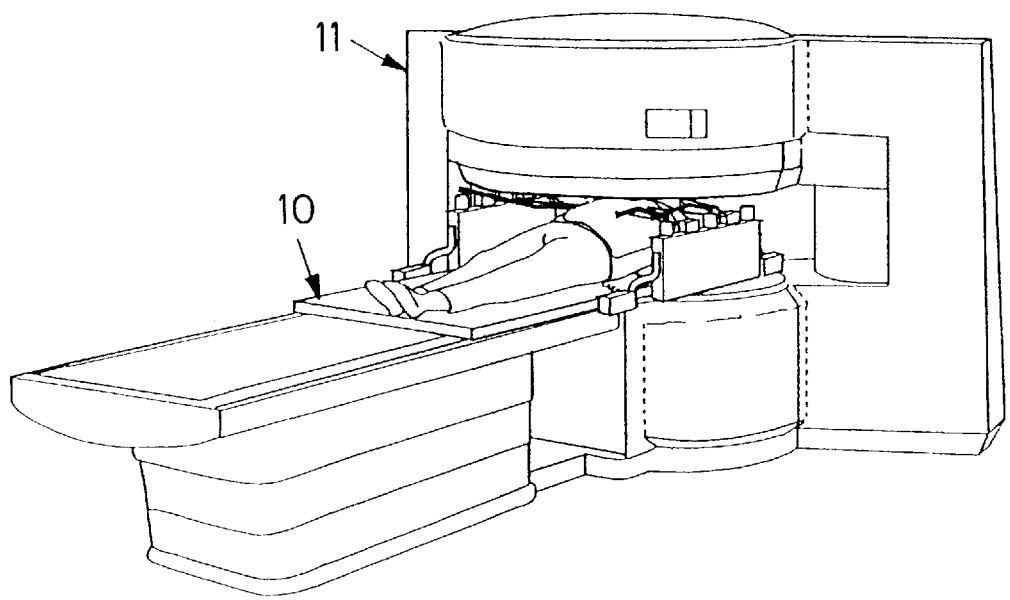
FIG. 4 is a diagram for explaining a state under the surgical operation in the first embodiment of the present invention.

After the setting of the devices to the patient is completed, the operating table is taken in the area made the object of measurement by the MRI apparatus so that the affected part is positioned at the area made the object of measurement (see FIG. 4). In this state, a cross-sectional image of the affected part is first measured by the MRI apparatus.

Thereby, a relation between the state of the affected part and the positions and postures of the attached surgical operating equipments is grasped or clarified. The surgical operating equipments are operated to move the endoscope relative to the affected part to a position at which the best observation of the affected part is attained. And, a medical care for the affected part is started.

In the case where the affected part is the interior of an internal organ, the ultrasonic scanner is brought into contact with the internal organ of interest while seeing an image from the endoscope. Thereby, an ultrasonic image is obtained. Further, the MRI apparatus is operated to obtain the grasp of a detailed positional relation and an MRI image of the affected part. A more accurate positional relation can be obtained by image-integrating the MRI image with the ultrasonic image.

The doctor performs a medical care while operating a master arm of the operation input device on the basis of the obtained positional information of the affected part to control an operating manipulator as a slave arm into a desired position/posture. On the way, if necessary, the measurement by the MRI apparatus is performed and the medical care is performed using the other surgical operating equipments freely while confirming the position and the state of the affected part.

The equipment management/control device 8 continually makes the communication of information with each equipment to make data exchange. Accordingly, necessary data is available from anywhere. Also, the equipment management/control device 8 monitors the state of each equipment always. In the case where an abnormality is generated in a specified equipment, the equipment management/control device 8 issues an alarm promptly and displays an abnormal location at the same time, so that the medical staffs are requested to cope with the abnormality. Thereby, the utilization of data is facilitated and the security of the surgical operating apparatus is improved.

In the case of a certain medical care, there are used not only a forceps and a laser knife but also a suture device, a suction pipe, a cleaning pipe, a sintering device, an ultrasonic equipment for medical care, and so forth. These are all used through conduit pipes provided in the operating manipulators or are used in place of the operating manipulators.

In a stage of time when the medical care action is completed or in the course of the medical care action, an MRI image is obtained by the MRI apparatus in order to confirm the success or failure and/or the effect of the medical care operation. The success or failure and/or the effect of the medical care can be confirmed from the flow of blood or the like as to whether or not the suture is complete, whether or not the function of the internal organ is started, and so forth. Also, there can be confirmed, for example, the case where there is bleeding in an unexpected area. Namely, there can be found out, for example, that bleeding out of the field of view of the endoscope which cannot be detected in the case where only the endoscope is used.

Thus, it is possible to perform the surgical operation while confirming the certainty of various measures taken in the course of the surgical operation. Thereby, it is possible to reduce the possibility of a re-operation which may result from inspection after the surgical operation. As a result, it is possible to reduce a load imposed on the patient. Also, since there can be found out that bleeding out of the field of view of the endoscope which is difficult to detect in the case where only the endoscope is used, the security of the surgical operation is improved.

It is possible for the surgical operator to easily make the change-over of image information by means of a pedal, key input, voice input or the like. Instructions for change-over may include the movement (or change) of the position/posture of an endoscope camera, the movement (or change) of the position/posture of the ultrasonic scanner, and the change of image data to be displayed, for example, a change in image of the MRI apparatus from transversal cross section to longitudinal cross section, a change from an image of the MRI apparatus to an image of the X-ray CT, the reduction of an image, the enlargement of an image, a change of a point of view, and a change in zoom point.

The doctor operates the manipulator with the operation being judged while seeing images from the endoscope, the ultrasonic scanner and the MRI apparatus. In order that the doctor is capable of performing a comfortable operation, the operation input device is designed such that the comparison of the manipulator with a surgical operating equipment is comprehensible. For example, even in the case where an image of the manipulator appearing in an endoscope image is positioned at the center, the operability is deteriorated if the posture does not correspond to a posture in the operation input device. Therefore, the operation input device is constructed such that a posture close to the posture of the manipulator on the endoscope as much as possible can be reemerged. For this purpose, a manipulator portion of the operation input device has a structure in which it can take the same posture as that of a slave manipulator on a display screen.

Supports, surgical operating equipments and so forth existing in a high-strength magnetic field of the MRI apparatus are made of materials such as feeble magnetic substance, ceramics or synthetic resin which are not influenced by a magnetic field even if it has a high strength and do not provide a hindrance to the measurement by the MRI apparatus. Similarly, actuators for driving such supports, surgical operating equipments and so forth are made of materials such as non-magnetic substance, feeble magnetic substance, ceramics, or resin and are driven on the basis of a driving principle such as oil pressure or hydraulic pressure other than electromagnetic force.

The functions of the surgical operating equipments constructed by the operational manipulators 4, the endoscope, the ultrasonic scanner, the MRI apparatus, and so forth are concentrically controlled by the equipment management/control device 8.

During MRI measurement, the operating manipulators 4, the surgical operating equipments, the endoscope and the ultrasonic scanner are controlled such that they are placed under electrically stopped conditions and mechanically locked non-operative conditions, in order to avoid influence which may be exerted on the result of detection by the MRI apparatus. On the other hand, even if an MRI measurement request is indicated by the doctor under the operation of the operating manipulators 4, the surgical operating equipments, the endoscope and the ultrasonic scanner, the indication of "UNDER OPERATION" and a warning are displayed to advise the doctor to stop the devices under operation. The equipment management/control device 8 makes a control of permitting the measurement by the MRI apparatus after the stopped conditions of the abovementioned devices are detected.

The equipment management/control device 8 monitors the state of each equipment in order that any abnormality can be detected always. Thereby, the reliability of the entire system is ensured.

A plurality of image monitors are prepared for each of the main operator and the assistant operator. Though the example of three display screens is shown, each screen is assigned for its parts or duties and designated for image data. In the case where one monitor of a multi-window type is used, there becomes vague or uncertain as to which window will which image data appear or hidden portions may be generated due to the overlapping of windows. The present embodiment provides a system in which such inconveniences are avoided to the utmost. One of the image monitors is a monitor which can provide a stereoscopic vision.

A further feature of the present embodiment lies in the arrangement of devices.

In the present embodiment, an operating position of the manipulator and a position subjected to medical care are separated from each other. Therefore, a position at which a surgical operator makes an operation input becomes important in considering the security. It is necessary to structure a system in which a surgical operator can act promptly while grasping the state of a patient and when a sudden change in condition of the patient occurs. In order that the doctor or operator can confirm the state of the patient with the minimum movement of the line of view, the devices are arranged such that each device certainly exists at a position from which the doctor can see through the patient.

Further, each device is arranged in an area having a magnetic field strength not higher than a predetermined strength (for example, 5 gauss) so that it is not affected by a magnetic field from the MRI apparatus and does not give an influence on the magnetic field. Thus, each device of a surgical operation supporting system is arranged in an area where a magnetic field strength in a magnetic field distribution around the MRI apparatus is not higher than the predetermined strength and at a position from which a doctor can see through a patient.

In FIG. 1, an area partitioning line 15 represents an equi-strength line of the predetermined magnetic field strength. With the equi-strength line 15 of the predetermined magnetic field strength taken as a boundary, each device is arranged outside of this boundary.

Thereby, the influence of a magnetic field on each device becomes below an allowable level and the doctor's attentiveness to the patient becomes maximum.

Each device referred to herein means not a surgical operating equipment, a support and so forth which acts under a high-strength magnetic field but a device such as the operation input device operation-inputted by the doctor, the device for monitoring an image from the endoscope 2, the ultrasonic scanner 3 or the MRI apparatus 1, the equipment management/control device 8 or the monitor 7 for anaesthetist which has no need to be placed directly under a magnetic field and a device such as a cathode-ray tube which is easily affected by a magnetic field.

The principle concerning the above-mentioned arrangement of each device similarly holds for other embodiments which will be mentioned later on.

The surgical operating apparatus according to the present invention includes at least one console. The surgical operating apparatus of the present embodiment has the main and auxiliary consoles 5 and 6. The main console 5 and a surgical operating position are arranged in the field of visual angle of the main operator while the auxiliary console 6 and a surgical operating position are arranged in the field of visual angle of the assistant operator.

In general, it is considered that the width of visual angle is 180 degrees, that is, 90 degrees from the direct front to each of right and left. At this time, if the console 5 or 6 is arranged so that the operating manipulator 4 exists on a side more back than a front face or the foremost portion of the console, there results in that the console 5 or 6 and the operating position are arranged in the field of visual angle of the operator 100 or 110. Namely, it is preferable that the operating manipulator 4 exists on the rear side of the console 5 relative to one-dotted chain line A shown in FIG. 1 or on the rear side of the console 6 relative to one-dotted chain line B.

In the case where the magnetic resonance imaging apparatus is an open gantry MRI apparatus having the cylindrical magnetic generators 12 which are provided parting up and down and the pillars 11 which support the magnetic generators 12 so that an interval therebetween is kept, the console 5 or 6 and an operating position are arranged in the angle of visibility of the operator 100 or 110 if the console 5 or 6 is arranged on the supporting device 9 side relative to the pillars 11 (or a line connecting the opposite pillars 11) in the longitudinal direction of the operating table 10.

In the above explanation, the width of visual angle is about 180 degrees and the console 5 or 6 and the operating position exist in this angle range. It is more preferable that the console 5 or 6 and the operating position are arranged in the range of 90 degrees. Thereby, it is not necessary to wave the head from side to side (or right and left) and the visibility is certainly improved.

Still more preferably, it is ideal that the console 5 or 6 and the operating position are aligned when seen from the surgical operator. At this time, it is preferable that the console 5 or 6 is small in height so that it does not shut off the view.

Further, the main console 5 and the auxiliary console 6 are arranged in an area limited depending on the strength of a magnetic field. For example, in the case where 5 gauss is the threshold value of the magnetic field strength, the area limited depending on the strength of a magnetic field corresponds to an area which has a magnetic field strength not higher than 5 gauss.

The monitor for anaesthetist, too, is arranged in an area limited depending on the strength of a magnetic field. Namely, the monitor for anaesthetist is arranged outside of an area which has a magnetic field strength higher than a predetermined magnetic field strength.

The predetermined magnetic field strength differs depending on a magnetic field strength allowed for each device.

Also, in the conventional MRI apparatus is accompanied with a room for operation and a room for measurement provided separately from each other. In the present embodiment, however, an operating unit for the MRI apparatus is arranged, without providing any special wall, in an operating room in which the MRI apparatus is disposed. Thereby, the doctor is easy to get near the patient in the case of emergency, the security is improved and the operability is improved.

Figure 5:
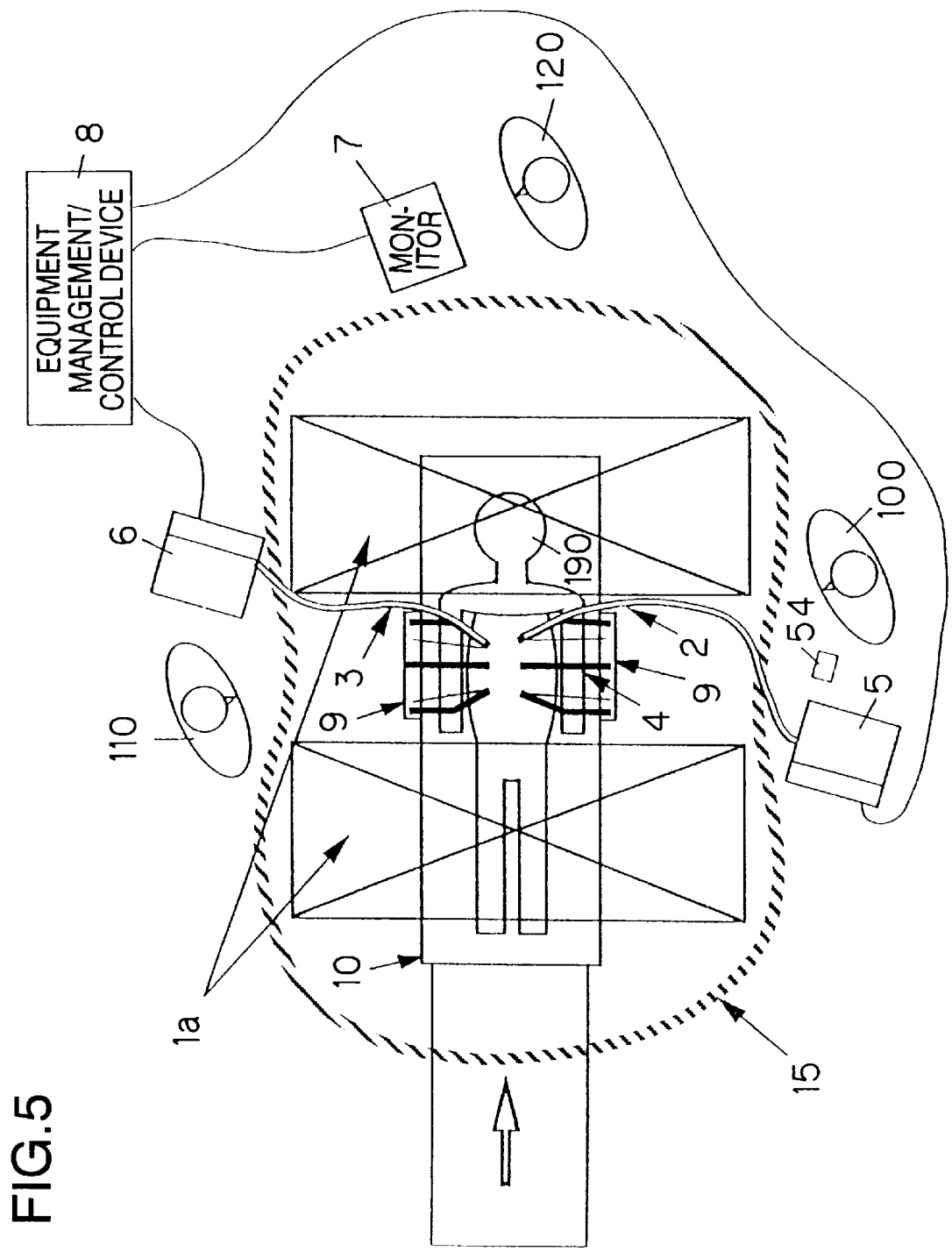
FIG. 5 is a diagram for explaining the arrangement in a second embodiment of the present invention.

FIG. 5 shows a second embodiment of the present invention. In this embodiment, an operating table is provided using an open gantry MRI apparatus separated right and left. A magnetic generator 1a is separated right and left, as shown in FIG. 5. Each of the separate generators 1a has a doughnut form, and a patient and the operating table are taken in a central portion of the doughnut form. Excepting the structure of the MRI apparatus, the other devices take constructions and arrangement similar to those in FIG. 1.

In this case, an ordinary surgical operation is also possible without a supporting device 9 and surgical operating equipments.

In this case, the attachment of each device for a low-incursion surgical operation can be made in such a manner that in a state in which the patient is fixed on the operating table, a surgical operating position of an affected part is located into an area made an object of measurement by the MRI apparatus by taking in the operating table and a supporting device and surgical operating equipments are thereafter attached.

For the MRI apparatus having such a construction as shown in FIG. 5, too, a console 5 or 6 is arranged in an area which has a magnetic field strength not higher than a predetermined magnetic field strength. Namely, the console is arranged outside of an area which has a magnetic field strength higher than the predetermined magnetic field strength.

In the separated open configured gantry MRI apparatus, a main operator 100 stands at a position on one of opposites sides of the operating table 10 in a space sandwiched between separate electromagnetic coils. An assistant operator 110 stands at a position on the other side opposite to the main operator 100 with the operating table 100 sandwiched therebetween. At this time, an anaesthetist doctor 120 stands at that position, on one side of the separate electromagnetic coils 1a, which is not in the way of the main operator 100 and the assistant operator 110 and at which the anaesthetist can see a patient 190. A medical information monitor 7 for the anaesthetist 120 is arranged such that it is easy to monitor the living body of the patient 190 and is placed at that position, in an area little influenced by a magnetic field and limited depending on a magnetic field strength, which does not interfere with the operators. In the present embodiment, the medical information monitor 7 is positioned on an extension line of the patient on his or her head side in a longitudinal direction of the operating table 10.

Figure 6:
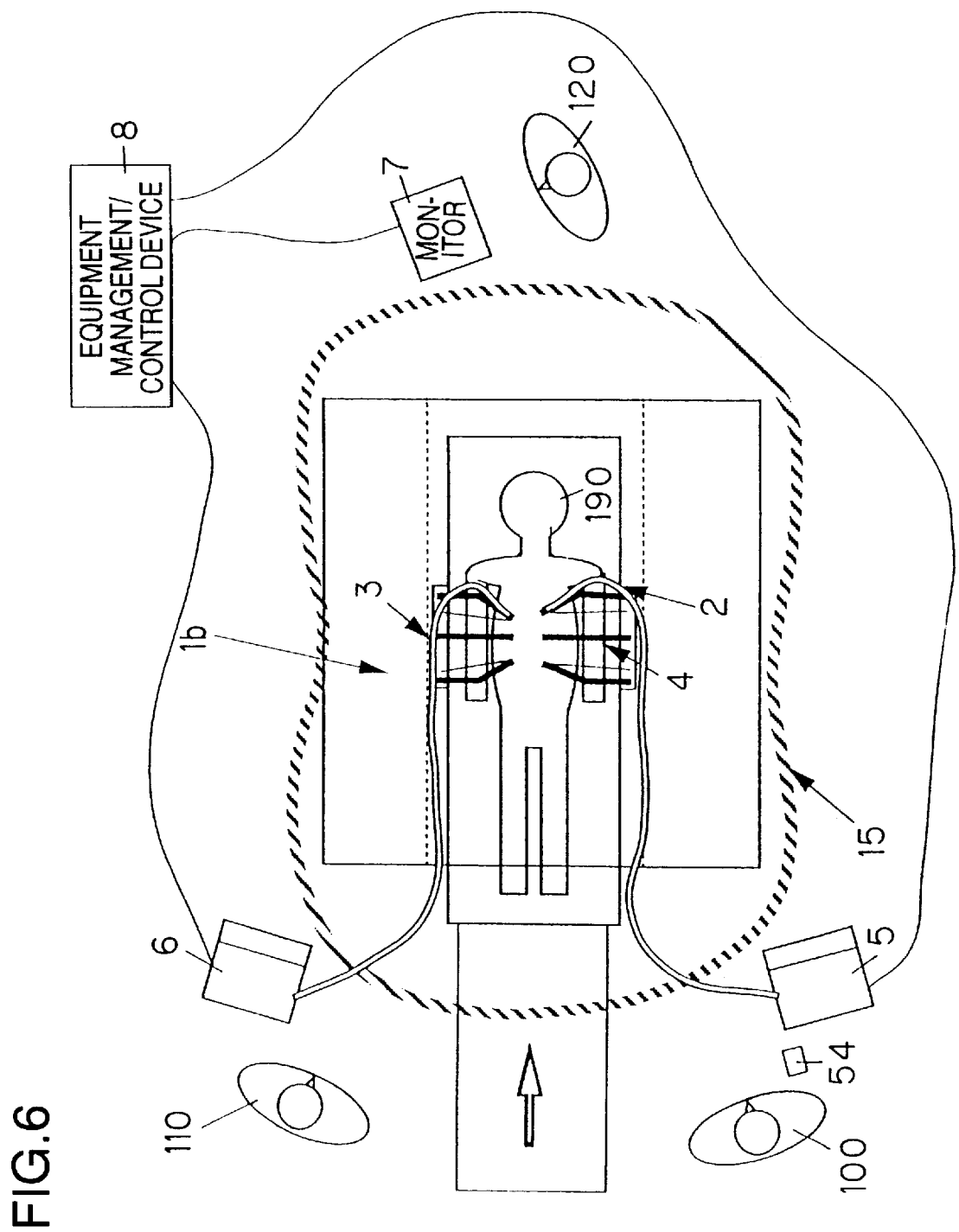
FIG. 6 is a diagram for explaining the arrangement in a third embodiment of the present invention.

FIG. 6 shows a third embodiment of the present invention. In this embodiment, an operating table is provided for a hollow-cylindrical MRI apparatus. Like the case of FIG. 1, an operating table is moved into an area made an object of measurement by the MRI apparatus after each equipment is attached in a state in which a patient is fixed on the operating table. This surgical operating apparatus can function in a manner quite similar to that in the case of FIG. 1.

For the MRI apparatus having such a construction as shown in FIG. 6, too, a console 5 or 6 is arranged in an area which has a magnetic field strength not higher than a predetermined magnetic field strength. Namely, the console is arranged outside of an area which has a magnetic field strength higher than the predetermined magnetic field strength.

Figure 7:
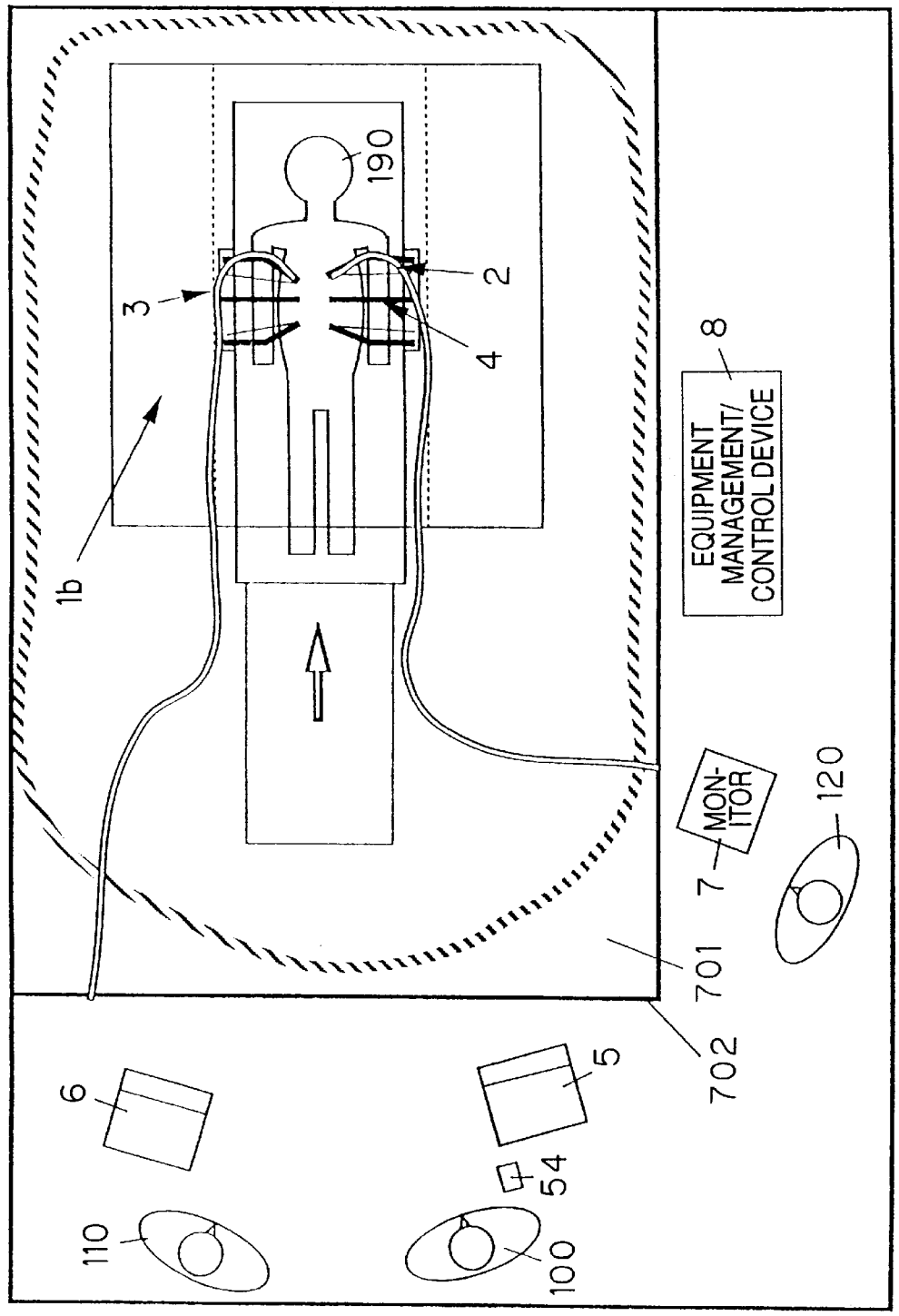
FIG. 7 is a diagram for explaining the arrangement in a fourth embodiment of the present invention.

FIG. 7 shows a fourth embodiment of the present invention. In this embodiment, an MRI apparatus is installed in a dedicated operating room 701. In the present embodiment, too, a console 5 for a main operator 100, a console 6 for an assistant operator 110 and a medical information monitor 7 for an anaesthetist 120 are arranged at positions from which the main operator 100, the assistant operator 110 and the anaesthetist 120 can see through a patient 190. For this purpose, a wall face 702 of the dedicated operating room 701 is provided with a window at a proper place or the whole of the wall face 702 is made transparent. Also, the wall face 702 of the operating room 701 is provided taking a magnetic field strength into consideration. At this time, the wall face 702 of the operating room 701 may be formed with a magnetic shielding effect. With a construction in which the MRI apparatus 1b is installed in the dedicated operating room 701 while equipments for controlling and operating surgical operating equipments are installed outside of the operating room 701, it becomes possible to control and operate the surgical operating equipments by even a person who undergoes no check as to whether he or she has no metallic substance thereon.

The present embodiment is particularly effective in the case where the strength of a magnetic field is high. The console is arranged in an area which has a magnetic field strength not higher than a predetermined magnetic field strength. Namely, the console is arranged outside of an area which has a magnetic field strength higher than the predetermined magnetic field strength.

In the present embodiment, in the case where the wall 702 is made by a flexible transparent curtain, it is possible to call the operator's attention to the approach to the MRI apparatus and there is no fear that the promptness upon approach of the operator to the patient in the case of emergency is deteriorated.

FIG. 8 shows a fifth embodiment of the present invention. The present embodiment is an example of the installation of an apparatus in the case where a surgical operation for the head is performed. Surgical operating equipments for head are attached on one end of an operating table in a longitudinal direction thereof. Further, the setting of the operating table and a patient for an MRI apparatus is made such that the surgical operating equipments can be arranged on a side of a larger opening, in order that the confirmation by doctors is more facilitated.

For the MRI apparatus in this case, too, a console is arranged in an area which has a magnetic field strength not higher than a predetermined magnetic field strength. Namely, the console is arranged outside of an area which has a magnetic field strength higher than the predetermined magnetic field strength. In this surgical operating apparatus, a main operator stands at a position which is on a wide open side and in an area limited depending on a magnetic field strength. Also, an assistant operator stands at a position on the wide open side or a back open side. An anaesthetist stands at a position on the back open side.

In each of the foregoing embodiments, the supporting device 9 and the surgical operating equipments are made of resin, ceramics or materials having a little influence by magnetism (such as aluminum, non-magnetic stainless steel or the like in the case of a metal).

The operating table may be replaced by a bed for inspection or may additionally be attached to the bed for inspection.

Next, a change-over between the measurement by the MRI apparatus and the operation of surgical operating equipments in the surgical operating apparatus according to the present invention will be described using FIG. 9. A control represented by a flow chart shown in FIG. 9 is performed in such a manner that the equipment management/control device 8 receives status information from each device such as the MRI apparatus 1, the master/slave manipulator controller 42, the ultrasonic scanner unit 3, the endoscope unit 2 or the like in accordance with a request from a doctor (for example, a switching operation of the console 5 or 6) and sends a control signal to each device.

The MRI apparatus generates a high-strength magnetic field. Therefore, if the measurement by the MRI apparatus is performed at the time of operation of surgical operating equipments, there may be generated a possibility that correct image information is not obtained due to the operation of the surgical operating equipments performed under measurement. Also, since the measurement by the MRI apparatus is used in combination with the endoscope unit, it is not required that the measurement by the MRI apparatus be continuously performed throughout the surgical operation. Accordingly, it is generally preferable that the measurement by the MRI apparatus and the use of the surgical operating equipments inclusive of manipulators are made exclusively from each other. However, a mode allowing the simultaneous use is prepared so far as the use is made in an extremely restricted place.

A flow chart upon exclusive use is shown by FIG. 9. Steps S901 and S904 to S908 show a judgement/control flow in the case where the measurement by the MRI apparatus is to be performed. Also, steps S903 and S909 to S913 show a control flow when the surgical operating equipment is to be used. "Y" represents the affirmative result of judgement and "N" represents the negative result of judgement.

First, the selection as the doctor's operation is made as to whether the measurement by the MRI apparatus is to be performed or the surgical operating equipment is to be used (steps S902 and S903). This selection is realized in such a manner that the doctor changes over a switch provided on the console (5 or 6) or the like. Non-manual change-over input means such as voice or speech may be used.

When the measurement by the MRI apparatus is selected, the equipment management/control device makes, on the basis of status information, the judgement of whether or not the MRI apparatus is under measurement (step S904). In the case where the MRI apparatus is under measurement, the measurement is continued, as it is (step S906). In the case where the MRI apparatus is not under measurement, the judgement of whether or not the surgical operating equipment is under use, is made on the basis of status information of the surgical operating equipment (step S905). In the case where the surgical operating equipment is under use, the equipment management/control device displays the state thereof to call the doctor's attention and performs an equipment use stopping process (step S907). After the confirmation of the stoppage of the surgical operating, the start of measurement by the MRI apparatus is displayed and a measuring operation sets in (step S908). In the case where the surgical operating equipment is not under use, the use of the surgical operating equipment is immediately started.

On the other hand, when the use of the surgical operating equipment is selected, the judgement is made of whether or not the surgical operating equipment is under use (step S909). In the case where the surgical operating equipment is under use, the use is continued (step 911). In the case where the surgical operating equipment is not under use, the the judgement is made of whether or not the MRI apparatus is under measurement (step S910). If the MRI apparatus is under measurement, a measurement stopping operation sets in (step S912). Thereafter, the use of the surgical operating equipment is started (step S913). If the MRI apparatus is not under measurement, the use of the surgical operating equipment is immediately started (step S913).

According to this flow chart, it is possible to control the measurement by the MRI apparatus and the use of the surgical operating equipment exclusively from each other. Though the shown flow assumes a state in which neither the MRI apparatus nor the surgical operating equipment is used, it is also possible to assume, as a usual state, a state in which either the MRI apparatus or the surgical operating equipment is used.

As an alternative to the shown example, a switch instructing the equipment management/control device to stop the measurement by the MRI apparatus may be provided on the console 5 or 6.

In each of the foregoing embodiments, the endoscope is used as local imaging means for a location to be subjected to surgical operation. However, another image take-in device may be used, so far as it can acquire an image as obtained by a TV camera, that is, an image (such as an endoscope image) as observed by the naked eyes. In any case, it is preferable that the imaging unit provides a clear image with which a surgical operation is easy to conduct.

With the surgical operating apparatus in the foregoing embodiment according to the present invention, since a surgical operation is performed while grasping the condition of an affected part by an external MRI apparatus, there is no exposure of medical staffs to X-rays.

Since supporting means can be moved in a longitudinal direction of an operating table, it is possible to easily set the supporting means to the optimum position as an operating position.

In the case of a certain location to be subjected to surgical operation, surgical operating equipments and the supporting means are disposed on one end of the operating table in the longitudinal direction. Thereby, it is possible to easily set the surgical operating equipments and the supporting means to the optimum position corresponding to the location to be subjected to surgical operation.

The supporting unit can be detached. This facilitates the cleaning and disinfection. Also, there can easily be offered for inspection as the MRI apparatus, thereby making it possible to improve the efficiency of use of the surgical operating apparatus.

With a construction in which the operating table can be taken in and out of an area made an object of measurement by the MRI apparatus, it is possible to easily locate an operating position of the affected part into the area made the object of measurement, thereby reducing a load imposed on the medical staffs.

With a construction in which not only an endoscope but also the MRI apparatus are used in combination while a low-incursion surgical operation is performed, it is possible to previously find out the bleeding outside of the field of view of the endoscope, thereby improving the security of the surgical operation.

With a surgical operation in which a doctor controls operating manipulators by an operation input device and a medical care itself is performed by the operating manipulators, there is a little chance of contact with humors, which is effective for the prevention of in-hospital infection or contagion.

The medical staffs can work while seeing an endoscope image, an ultrasonic image and an MRI image. Also, enormous information obtained by inspection before a surgical operation can be confirmed by an image integrating device on occasion under operation. Thereby, it is possible to improve the security of the surgical operation.

Since each equipment is continually monitored by an equipment management/control device, the security can be ensured.

Since a surgical operation is performed while grasping the condition of an affected part by use of the MRI apparatus from the exterior, it is possible to perform the operation while confirming the medical effect of the operation. Thereby, the reliability of the surgical operation is improved.

Since a high-reliability low-incursion surgical operation is enabled, the term of hospital treatment can be shortened, thereby making it possible to reduce medical fee as the whole.

Since an operation for medical care based on manipulators can be performed, there are effects for the prevention of infection associated with a surgical operation and the prevention of in-hospital infection.

Since a surgical operation under the MRI apparatus can be performed low-incursively, there are provided the effects of a reduction in medical fee resulting from the shortening of the term of hospital treatment, a personnel saving resulting from the use of the machine, the generalization of an advanced technique for medical care, and so forth.

The doctor can work with no need to get near the patient and the MRI apparatus, thereby making it possible to reduce the influence of a high-strength magnetic field. Further, the doctor can takes a position from which he or she can see through the patient and each device is arranged in a area which has a magnetic field strength not higher than a predetermined magnetic field strength. Thereby, the influence of a magnetic field on each device is minimized and the doctor's attentiveness becomes maximum to the patient.

Each device referred to herein means not a surgical operating equipment, a support and so forth which acts under a high-strength magnetic field but a device such as the operation input device operation-inputted by the doctor, a device for monitoring an image from the endoscope, the ultrasonic scanner or the MRI apparatus, the equipment management/control device or a monitor for anaesthetist which has no need to be placed directly under a magnetic field and a device such as a cathode-ray tube which is easily affected by a magnetic field.

What is claimed is:

1. A surgical operating apparatus comprising an operating manipulator provided with surgical operating equipment for operating inside of an object, operation input means for operating said operating manipulator, measurement means for measuring at least one of an operating area inside of the object and an operating area of said operating manipulator operating inside of the object, an operation table on which said object can be laid, and a magnetic resonance imaging apparatus for measuring an area wider than the measured operating area of said measurement means, wherein at least one of said magnetic resonance imaging apparatus and said operation table is relatively movable to a position at which said magnetic resonance imaging apparatus can measure an area of said operation table, and said operating manipulator is movable with respect to said operation table.

2. A surgical operating apparatus according to claim 1, wherein said operation table has at least one of a support for supporting said operating manipulator and a display means for displaying information from said magnetic resonance imaging apparatus, said support being installed at a side edge portion of said operating table in a longitudinal direction of said operating table.

3. A surgical operating apparatus according to claim 2, wherein said operation table has said support.

4. A surgical operating apparatus according to claim 3, wherein said support is removable and attachable.

5. A surgical operating apparatus according to claim 1, wherein said operating manipulator is movable with respect to said operation table in a longitudinal direction of said operation table.

6. A surgical operating apparatus according to claim 2, wherein said operating manipulator is movable with respect to said operation table in a longitudinal direction of said operation table.

7. A surgical operating apparatus according to claim 4, wherein said operating manipulator is movable with respect to said operation table in a longitudinal direction of said operation table.

8. A surgical operating apparatus according to claim 2, wherein said support is locatable between said operation table and operating manipulator.

9. A surgical operating apparatus according to claim 3, wherein said support is locatable between said operation table and operating manipulator.

10. A surgical operating apparatus according to claim 4, wherein said support is locatable between said operation table and operating manipulator.

11. A surgical operating apparatus according to claim 6, wherein said support is locatable between said operation table and operating manipulator.

12. A surgical operating apparatus according to claim 1, further comprising an adjusting means for exclusively performing a measurement using one of said magnetic resonance apparatus and operation of said surgical operating equipment.

13. A surgical operating apparatus according to claim 2, further comprising an adjusting means for exclusively performing a measurement using one of said magnetic resonance apparatus and operation of said surgical operating equipment.

14. A surgical operating apparatus according to claim 4, further comprising an adjusting means for exclusively performing a measurement using one of said magnetic resonance apparatus and operation of said surgical operating equipment.

15. A surgical operating apparatus according to claim 5, further comprising an adjusting means for exclusively performing a measurement using one of said magnetic resonance apparatus and operation of said surgical operating equipment.

16. A surgical operating apparatus according to claim 8, further comprising an adjusting means for exclusively performing a measurement using one of said magnetic resonance apparatus and operation of said surgical operating equipment.

* * * * *